US00PP21230P2

(12) United States Plant Patent
Lemon

(10) Patent No.: US PP21,230 P2
(45) Date of Patent: Aug. 24, 2010

(54) ***GERANIUM* PLANT NAMED 'OGLGER14007'**

(50) Latin Name: *Pelargonium×hortorum*
Varietal Denomination: Oglger14007

(75) Inventor: David G. Lemon, Lompoc, CA (US)

(73) Assignee: Ecke Geraniums, LLC, Encinitas, CA (US)

( * ) Notice: Subject to any disclaimer, the term of this patent is extended or adjusted under 35 U.S.C. 154(b) by 0 days.

(21) Appl. No.: 12/386,342

(22) Filed: Apr. 15, 2009

(51) Int. Cl.
*A01H 5/00* (2006.01)

(52) U.S. Cl. ..... Plt./330

(58) Field of Classification Search ..... Plt./330, Plt./325

See application file for complete search history.

(56) References Cited

OTHER PUBLICATIONS

UPOV Plant Variety Database 2009/06 search for cultivar OGLGER14007 p.1.*

* cited by examiner

*Primary Examiner*—Annette H Para
(74) *Attorney, Agent, or Firm*—C.A. Whealy

(57) ABSTRACT

A new and distinct cultivar of Zonal *Geranium* plant named 'Oglger14007', characterized by its compact, upright to outwardly spreading and mounded plant habit; freely branching habit; freely and early flowering habit; dark green-colored leaves; bright red-colored flowers; and good garden performance.

1 Drawing Sheet

Botanical designation: *Pelargonium×hortorum*.
Cultivar denomination: 'Oglger14007'.

BACKGROUND OF THE INVENTION

The present invention relates to a new and distinct cultivar of Zonal *Geranium* plant, botanically known as *Pelargonium×hortorum*, and hereinafter referred to by the name 'Oglger14007'.

The new Zonal *Geranium* plant is a product of a planned breeding program conducted by the Inventor in Lompoc, Calif. The objective of the breeding program is to create new compact Zonal *Geranium* cultivars with dark green-colored leaves and attractive flower coloration.

The new Zonal *Geranium* plant originated from a cross-pollination made by the Inventor in June, 2002 in Lompoc, Calif. of a proprietary selection of *Pelargonium×hortorum* identified as code number 8824, not patented, as the female, or seed, parent with *Pelargonium×hortorum* 'Grand Prix', not patented, as the male, or pollen, parent. The new Zonal *Geranium* was discovered and selected by the Inventor as a single flowering plant from within the progeny of the stated cross-pollination in a controlled greenhouse environment in Connellsville, Pa. in March, 2004.

Asexual reproduction of the new Zonal *Geranium* plant by vegetative terminal cuttings in a controlled greenhouse environment in Connellsville, Pa. since March, 2005, has shown that the unique features of this new Zonal *Geranium* plant are stable and reproduced true to type in successive generations.

SUMMARY OF THE INVENTION

Plants of the new Zonal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Oglger14007'. These characteristics in combination distinguish 'Oglger14007' as a new and distinct cultivar of Zonal *Geranium:*

1. Compact, upright to outwardly spreading and mounded plant habit.
2. Freely branching habit.
3. Freely and early flowering habit.
4. Dark green-colored leaves.
5. Bright red-colored flowers.
6. Good garden performance.

Plants of the new Zonal *Geranium* differ primarily from plants of the female parent selection in flowering time as plants of the new Zonal *Geranium* flower earlier than plants of the female parent selection. In addition, flower color of plants of the new Zonal *Geranium* is brighter than flower color of plants of the female parent selection.

Plants of the new Zonal *Geranium* differ primarily from plants of the male parent, 'Grand Prix', in leaf color as plants of the new Zonal *Geranium* have darker green-colored leaves.

Plants of the new Zonal *Geranium* can be compared to plants of *Pelargonium×hortorum* 'Tango', disclosed in U.S. Plant Pat. No. 5,933. In side-by-side comparisons conducted in Encinitas, Calif., plants of the new Zonal *Geranium* differed primarily from plants of 'Tango' in plant size as plants of the new Zonal *Geranium* were not as compact as plants of 'Tango'.

BRIEF DESCRIPTION OF THE PHOTOGRAPHS

The accompanying colored photographs illustrate the overall appearance of the new Zonal *Geranium* plant, showing the colors as true as it is reasonably possible to obtain in colored reproductions of this type.

Colors in the photographs may differ slightly from the color values cited in the detailed botanical description which accurately describe the colors of the new Zonal *Geranium* plant.

The photograph at the bottom of the sheet comprises a side perspective view of a typical flowering plant of 'Oglger14007' grown in a container.

The photograph at the top of the sheet is a close-up view of a typical inflorescence of 'Oglger14007'.

DETAILED BOTANICAL DESCRIPTION

The aforementioned photographs and following observations, measurements and values describe plants grown in Encinitas, Calif. in a polyethylene-covered greenhouse during the spring and under conditions which closely approximate Zonal *Geranium* commercial production. During the production of the plants, day temperatures averaged 24° C., night temperatures averaged 19° C. and light levels averaged 4,000 foot-candles. Plants had been growing for 15 weeks when the photographs and the description were taken. In the detailed description, color references are made to The Royal Horticultural Society Colour Chart, 2001 Edition, except where general terms of ordinary dictionary significance are used.

Botanical classification: *Pelargonium×hortorum* 'Oglger14007'.

Parentage:

*Female, or seed, parent.*—Proprietary selection of *Pelargonium×hortorum* identified as code number 8824, not patented.

*Male or pollen parent.*—*Pelargonium×hortorum* 'Grand Prix', not patented.

Propagation:

*Type.*—By vegetative terminal cuttings.

*Time to initiate roots, summer.*—About ten days at temperatures of 20° C.

*Time to initiate roots, winter.*—About two weeks at temperatures of 16° C.

*Time to produce a rooted young plant, summer.*—About four weeks at temperatures of 20° C.

*Time to produce a rooted young plant, winter.*—About four weeks at temperatures of 16° C.

*Root description.*—Fine, fibrous; white in color.

*Rooting habit.*—Freely branching.

Plant description:

*General appearance.*—Compact, upright to outwardly spreading and mounding plant habit; densely foliated.

*Growth and branching habit.*—Moderately vigorous growth habit. Freely branching habit; about five primary lateral branches develop per plant.

*Plant height, to top of umbels.*—About 27 cm.

*Plant height, to top of foliar plane.*—About 15 cm.

*Plant diameter (spread).*—About 26 cm.

*Lateral branches.*—Length: About 10.5 cm. Diameter: About 7 mm. Internode length: About 1.5 cm. Texture: Pubescent. Strength: Strong. Color: Close to 146C.

Foliage description:

*Arrangement.*—Alternate; simple.

*Length.*—About 6.5 cm.

*Width.*—About 7.6 cm.

*Shape.*—Reniform.

*Apex.*—Rounded.

*Base.*—Cordate.

*Margin.*—Sinuate, erose.

*Venation pattern.*—Palmate.

*Texture, upper and lower surfaces.*—Pubescent.

*Color.*—Developing leaves, upper surface: Close to 144A. Developing leaves, lower surface: Close to 147C. Fully expanded leaves, upper surface: Close to 146A; venation, close to 146B. Fully expanded leaves, lower surface: Close to 147B; venation, close to 147C. Zonation pattern: Location of zone from margin: About 1.4 cm. Width: About 6.5 mm. Color: Close to 147A.

*Petiole.*—Length: About 5.8 cm. Diameter: About 2.5 mm. Texture, upper and lower surfaces: Pubescent. Color, upper and lower surfaces: Close to 146A.

Flower description:

*Flower arrangement.*—Rotate flowers arranged in hemispherical umbels arising from apical leaf axils. Umbels displayed above the foliage on strong peduncles. Flowers face upright to outward; flowers slightly cupped becoming flatter with development.

*Fragrance.*—None detected.

*Quantity of flowers.*—Freely flowering habit; about 30 flowers and flower buds per umbel; about four to five umbels per plant at one time.

*Flowering season.*—In Encinitas, Calif., flowering is continuous during the spring and summer.

*Flower longevity.*—Individual flowers last about one week on the plant; flowers persistent.

*Umbel height.*—About 5.8 cm.

*Umbel diameter.*—About 8.4 cm.

*Flower diameter.*—About 4 cm.

*Flower depth (height).*—About 2.1 cm.

*Flower buds.*—Length: About 1.5 cm. Diameter: About 7 mm. Shape: Elliptic to obovate. Color: Close to 42A to 42B.

*Petals.*—Quantity per flower: About ten to eleven in two whorls. Length: About 2 cm to 2.3 cm. Width: About 1.1 to 2.1 cm. Shape: Obovate. Apex: Rounded. Base: Attenuate. Margin: Entire. Texture, upper and lower surfaces: Smooth, glabrous; velvety. Color: When opening, upper surface: Close to 45A. When opening, lower surface: Close to 44A. Fully opened, upper surface: Close to 44B; at the base, close to 56D; venation, close to 46B; color does not fade with development. Fully opened, lower surface: Close to 44C; at the base, close to 56D; venation, close to 46D.

*Sepals.*—Quantity per flower: Five, arranged in a single whorl. Length: About 1.1 cm. Width: About 2 mm. Shape: Narrowly elliptical. Apex: Acuminate. Base: Attenuate. Margin: Entire. Texture, upper surface: Smooth, glabrous. Texture, lower surface: Pubescent. Color, upper surface: Close to 146D. Color, lower surface: Close to 146B tinted with close to 183D.

*Peduncle (umbel stem).*—Length: About 17 cm. Diameter: About 5 mm. Strength: Strong. Texture: Pubescent. Color: Close to 148A occasionally tinted with close to 183C.

*Pedicel (individual flower stem).*—Length: About 2.7 cm. Diameter: About 1.5 mm. Strength: Strong. Texture: Pubescent. Color: Close to 183C.

*Reproductive organs.*—Androecium: Stamen quantity per flower: About eight. Anther size: About 1 mm by 2 mm. Anther shape: Oblong. Anther color: Close to 182B. Pollen amount: Scarce. Pollen color: Close to 28A. Gynoecium: Pistil quantity per flower: One. Pistil length: About 9 mm. Stigma shape: Split into five parts, star-shaped. Stigma color: Close to 53B. Style length: About 2.5 mm. Style color: Close to 53D. Ovary color: Close to 194C.

*Seed/fruit.*—Seed and fruit development have not been observed.

Disease/pest resistance:

Plants of the new Zonal *Geranium* have not been observed to be resistant to pathogens and pests common to Zonal *Geraniums.*

Garden performance:

Plants of the new Zonal *Geranium* have been observed to tolerate rain, wind, and temperatures ranging from about 4° C. to about 35° C. and have demonstrated good garden performance.

It is claimed:

1. A new and distinct Zonal *Geranium* plant named 'Oglger14007' as illustrated and described.

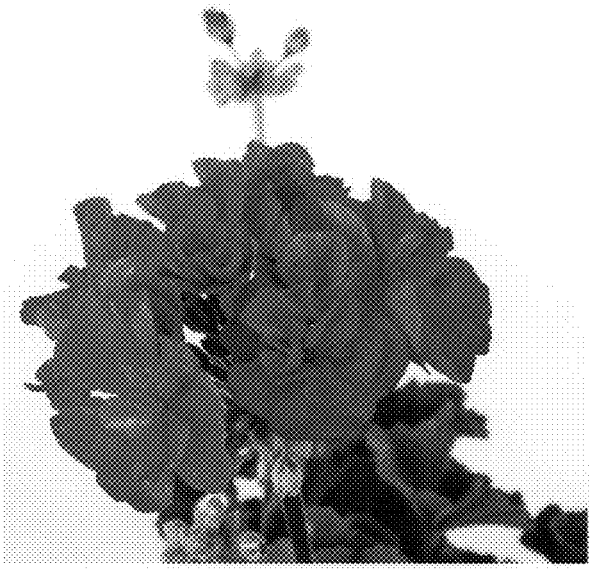
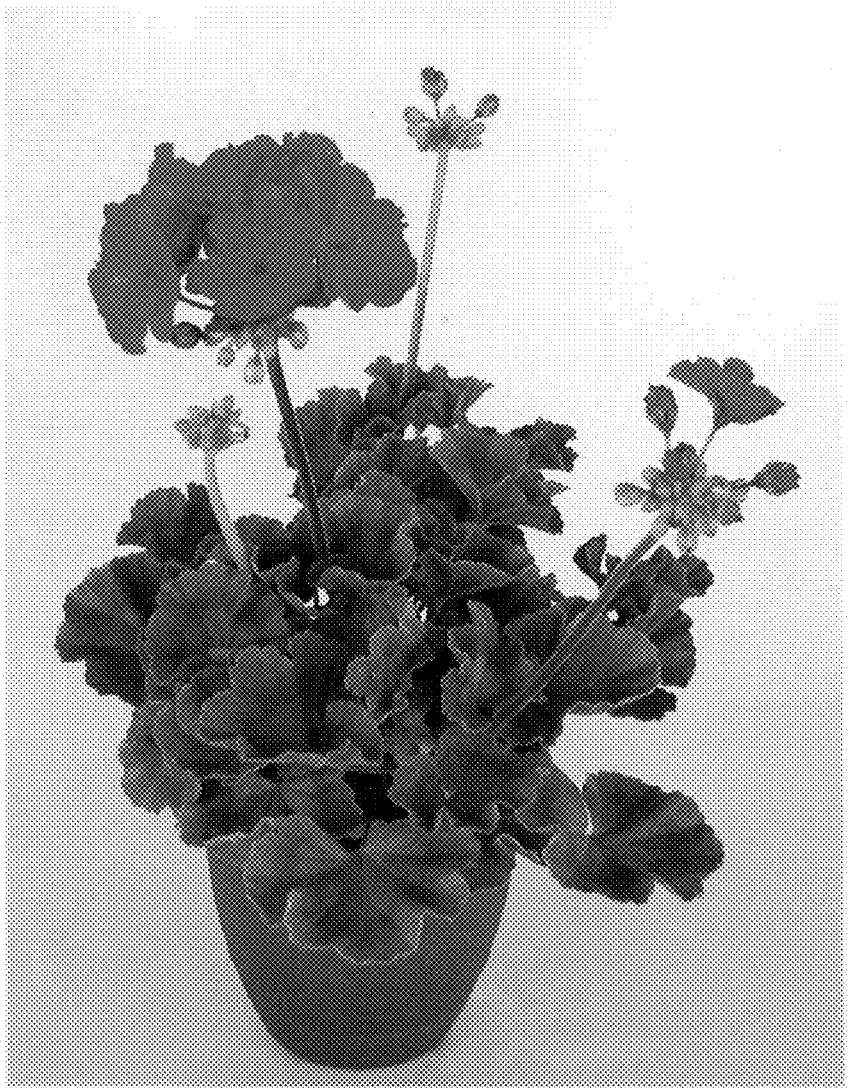

* * * * *